(12) United States Patent
Lynn

(10) Patent No.: US 6,749,672 B2
(45) Date of Patent: Jun. 15, 2004

(54) SCENTING DEVICE FOR AIR FLOW APPARATUS

(76) Inventor: Cathy A. Lynn, 8112 S. Lamon Ave., Burbank, IL (US) 60459

( * ) Notice: Subject to any disclaimer, the term of this patent is extended or adjusted under 35 U.S.C. 154(b) by 0 days.

(21) Appl. No.: 09/846,800

(22) Filed: Apr. 30, 2001

(65) Prior Publication Data
US 2002/0157540 A1 Oct. 31, 2002

(51) Int. Cl.$^7$ ................................................ A61L 9/12
(52) U.S. Cl. ........................ 96/222; 34/96; 422/123
(58) Field of Search ........................ 96/222; 428/905; 261/100, DIG. 17; 34/96, 390; 422/120, 123; 239/60

(56) References Cited

U.S. PATENT DOCUMENTS

| 4,028,073 | A | * | 6/1977 | Swaim | 206/482 |
|---|---|---|---|---|---|
| 4,043,776 | A | | 8/1977 | Orel | |
| 4,065,262 | A | * | 12/1977 | Petroff | 239/289 |
| 4,257,787 | A | * | 3/1981 | Taylor | 422/123 |
| 4,563,333 | A | * | 1/1986 | Frigon | 422/122 |
| 4,597,781 | A | | 7/1986 | Spector | |
| 4,604,114 | A | | 8/1986 | Ward | |
| 4,835,879 | A | * | 6/1989 | Egelstad | 34/72 |
| 5,087,273 | A | * | 2/1992 | Ward | 239/55 |
| 5,240,487 | A | * | 8/1993 | Kung | 261/DIG. 88 |
| 5,273,690 | A | * | 12/1993 | McDowell | 206/532 |
| 5,415,675 | A | | 5/1995 | Powers et al. | |
| 5,460,787 | A | * | 10/1995 | Colon | 239/55 |
| 5,572,800 | A | * | 11/1996 | West | 34/390 |
| 5,649,370 | A | * | 7/1997 | Russo | 34/97 |
| 5,698,166 | A | * | 12/1997 | Vick et al. | 261/30 |
| 5,701,681 | A | * | 12/1997 | Wonka et al. | 34/96 |
| 5,704,832 | A | * | 1/1998 | Borrell | 261/100 |
| 5,820,791 | A | * | 10/1998 | Canale | 239/54 |
| 6,117,218 | A | | 9/2000 | Snyder et al. | |
| 2002/0139251 | A1 | * | 10/2002 | Simmons | 96/134 |
| 2002/0197187 | A1 | * | 12/2002 | Murray | 422/124 |
| 2003/0159306 | A1 | * | 8/2003 | Yeung | 34/96 |

* cited by examiner

Primary Examiner—Frank M. Lawrence
(74) Attorney, Agent, or Firm—Milord A. Keshishian

(57) ABSTRACT

A scenting device for use with airflow conduits. The scenting device has a porous first member enclosed at a periphery thereof by a frame. A mounting means is used to removably yet securely attach the scenting device to an air filter or ventilation cover in existing heating, ventilating, air conditioning systems in addition to use with hair dryers.

13 Claims, 3 Drawing Sheets

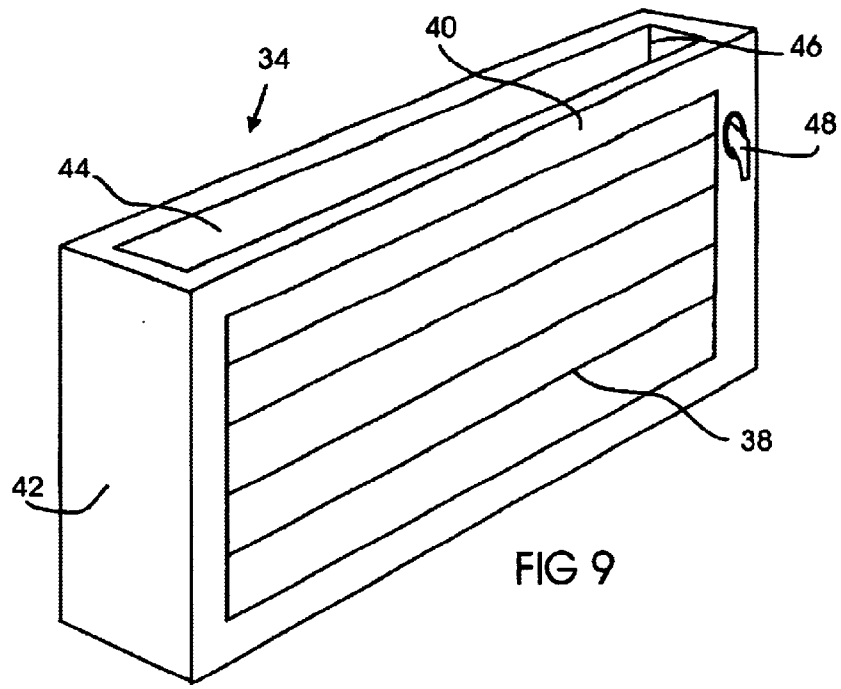
FIG 9
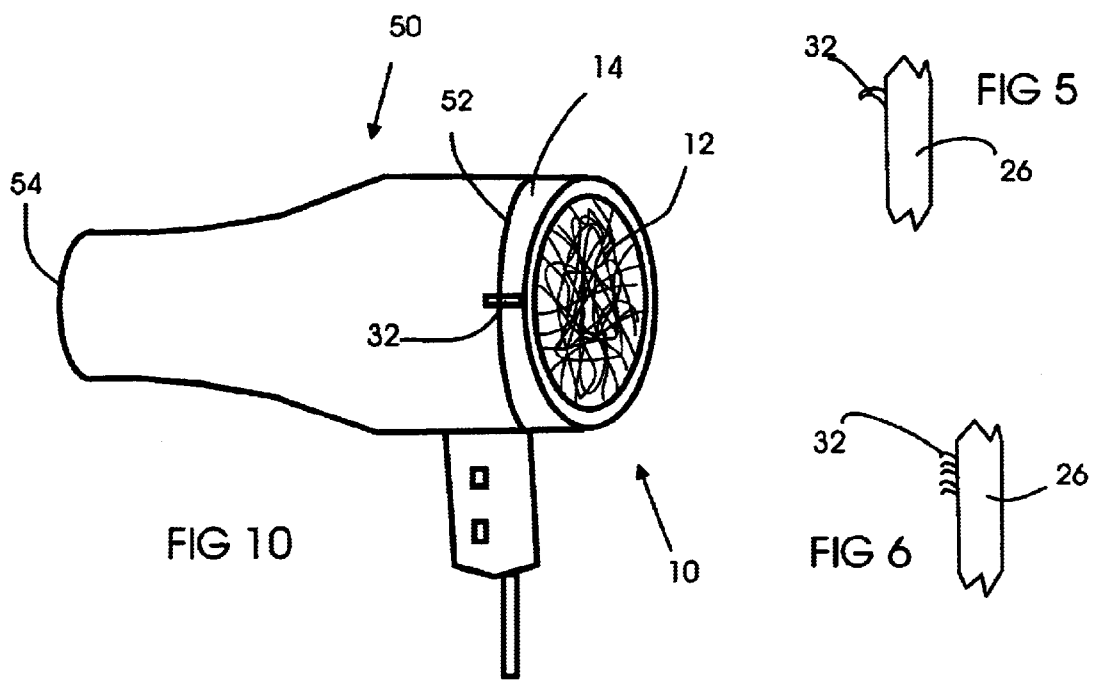
FIG 10
FIG 5
FIG 6

SCENTING DEVICE FOR AIR FLOW APPARATUS

FIELD OF THE INVENTION

This invention relates to the field of air fresheners in general, and particularly to an air freshener device that is adapted to function with an air filter or a ventilation cover installed on various apparatuses to provide fresh, clean and scented air into the environment.

BACKGROUND OF THE INVENTION

Sterilizing air filters have been known in the art where the filters have been placed in heating, air-conditioning or ventilating systems in order to sterilize or remove particles from the air flowing therethrough. In addition, fragrance emitting compositions and devices are known in the art. However, there has not been an effective combination of the two devices to date.

For example, U.S. Pat. No. 6,117,218 to Snyder et al. discloses a scenting device for attachment to an air filter in a heating, ventilating, or air conditioning (HVAC) system. However, the Snyder device is impermeable to air which flows through the HVAC system. Snyder's device provides a plurality of gel containing compartments which are mounted on a solid surface that is in turn attached to an air filter. In such an arrangement, the impermeable nature of the mounting material may create excessive resistance to flow in the air circulation system and result in excessive pressure drop and an inadequate air flow rate.

U.S. Pat. No. 5,415,675 to Powers et al. discloses a fragrant sponge strip which is mounted onto an air filter. Powers' fragrant sponge strip has a plurality of hooks that are located on the outer edge of the sponge and requires that the filter itself have apertures that are adapted to receive the hooks. Accordingly, the Powers sponge strip is not adapted to be used with varying filter systems and may only be used with filters that have the corresponding apertures for receiving the hooks of the sponge.

U.S. Pat. No. 4,597,781 to Spector discloses an air purifier unit which must be purchased as a whole and cannot be used with preexisting HVAC systems. Spector's air purifier utilizes a plurality of consecutively positioned filters that are progressively graded to remove finer particles. The last filter is adapted to receive an aromatic liquid thereon and thus the resulting air therefrom is fragrant. However, the Spector unit cannot be installed onto a preexisting filter that is currently installed on an HVAC system.

U.S. Pat. No. 4,604,114 to Ward discloses a fragrant scented air filter. The air filter consists of padding which is enclosed by a surrounding border. Fragrant rods are enclosed within the padding itself and span between opposing borders. Accordingly, if the fragrance is depleted, the entire filter itself must be replaced and unreasonable expenses incurred if the filter itself is still functional.

U.S. Pat. No. 4,043,776 to Orel discloses a filter for use by smokers. Orel's device consists of a shroud that is placed over an ashtray and contains a fan therein to draw the smoke contaminated air up through a filter which absorbs the contaminants. In addition, the absorbent filter contained therein may be impregnated with a perfume to enhance the fragrance of the air flowing therethrough. However, Orel's device is not adapted to filter the air outside of the shroud which encloses the ashtray and is not capable of use with preexisting filters.

The prior art does not address the need for a fragrant containing device that is adapted for use on preexisting filters currently in use. Therefore, there remains a long standing and continuing need for an advance in the art of fragrant air filters that is simpler in both design and use, is more economical, efficient in its construction and use, and eliminates the need to purchase an unnecessary unit.

SUMMARY OF THE INVENTION

Accordingly, it is a general object of the present invention to overcome the disadvantages of the prior art.

In particular, it is an object of the present invention to provide a scenting device that is adaptable for use with any HVAC system.

It is another object of the present invention to provide a scenting device that can be mounted on preexisting filters so that a fresh clean scent can mix with the filtered air passing through.

It is another object of the present invention to provide a scenting device that may be easily replaced.

It is another object of the present invention to provide a scenting device that is economical in cost to manufacture and use.

It is another object of the present invention to provide a scenting device that is easy to manufacture and use.

It is another object of the present invention to provide a scenting device that does not significantly reduce the air pressure or air flow passing through a filter.

It is yet another object of the present invention to provide a scenting device that can be used with preexisting blow dryers.

In keeping with the principles of the present invention, a unique scenting device is herein disclosed. The scenting device has a first member that is of a porous nature and is adapted to either have the scented element applied thereto through immersing the same therein or enclosing scenting elements within the first member. The first member is enclosed peripherally by a rigid frame. In one preferred embodiment, an attaching means may be provided on the frame to attach the device to a filter or a vent cover over an airflow conduit.

In an alternate embodiment, a mounting means of a generally "U" shape is provided that has inwardly facing groove to slideably receive the frame of scenting device therein. The attaching means is then applied to the mounting means and attaches the same to the air filter or vent cover. In such an arrangement, the scenting device may be removed and replaced while the mounting means may permanently be left in place.

In an alternate embodiment, the ventilation cover is modified to receive the scenting device directly therein in a removable yet permanent manner.

Such stated objects and advantages of the invention are only examples and should not be construed as limiting the present invention. These and other objects, features, aspects, and advantages of the invention herein will become more apparent from the following detailed description of the embodiments of the invention when taken in conjunction with the accompanying drawings and the claims that follow.

BRIEF DESCRIPTION OF THE DRAWINGS

It is to be understood that the drawings are to be used for the purposes of illustration only and not as a definition of the limits of the invention.

In the drawings, wherein similar reference characters denote similar elements throughout the several views:

FIG. 5 is an elevational partial view of the scenting device illustrating one preferred attaching mechanism.

FIG. 6 is an elevational partial view of the scenting device illustrating another preferred attaching mechanism.

FIG. 9 is a perspective view of a vent cover that is adapted to receive a scenting device directly therein.

FIG. 10 is a perspective view of a hair dryer adapted to receive a scenting device thereon.

DETAILED DESCRIPTION OF THE INVENTION

Figure 1:
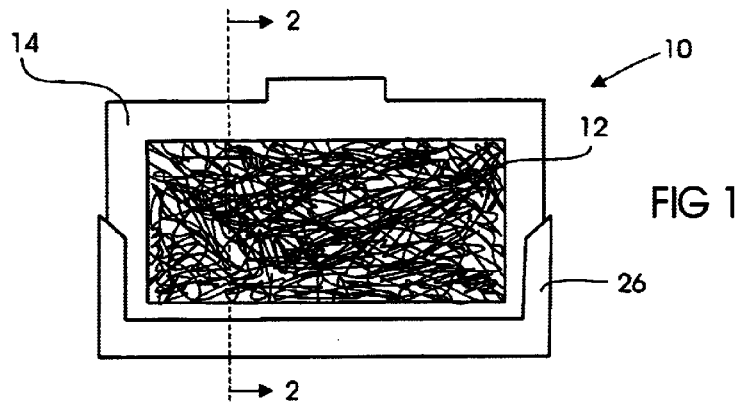
FIG. 1 is a frontal view of the scenting device in accordance with one preferred embodiment of the present invention.

Referring to FIG. 1, therein is illustrated a scenting device 10 that is adapted to function with existing heating, air conditioning and venting systems. Scenting device 10 is generally polygonal in shape and is relatively planar in nature in one preferred embodiment, however it is to be understood that device 10 may be circular or any other desired shape. Device 10 has a first member 12 which is air permeable in nature and porous. In a preferred embodiment, the first member 12 may be a fibrous filtering material, such as fiberglass, however it is to be understood that the composition thereof is not limited thereto. The first member 12 has a frame 14 around the periphery thereof thereby enclosing the same.

Figure 2:
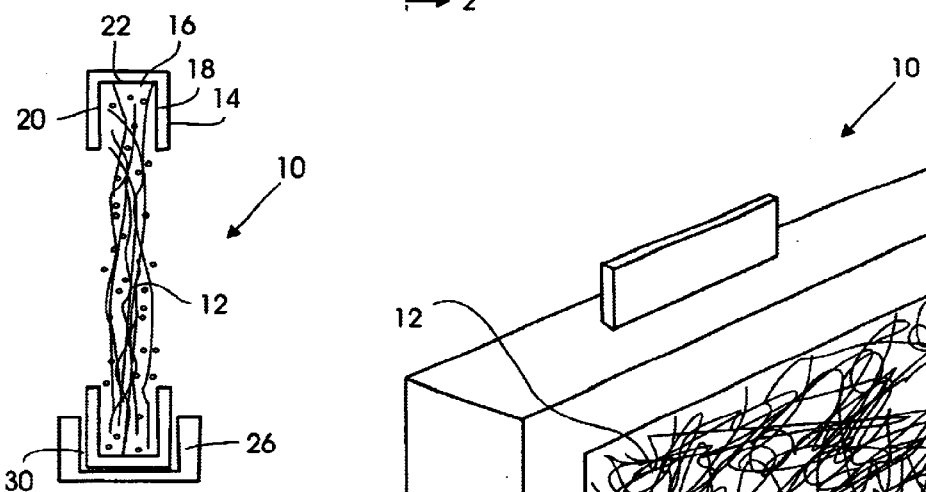
FIG. 2 is a cross sectional view of the scenting device taken along line 2—2 of FIG. 1.
Figure 3:
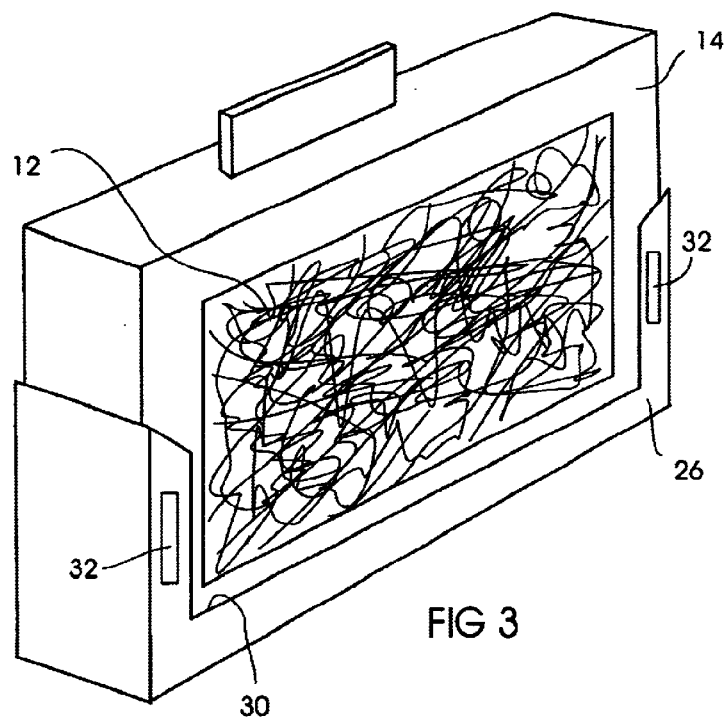
FIG. 3 is a perspective rearward view of the scenting device.

Now also referring to FIGS. 2 and 3, the frame 14 is preferably constructed of a substantially rigid yet light weight material such as paper based material or plastics. The frame 14 has an inwardly opening channel 16 having a first wall 18 and a second wall 20 interconnected by a floor 22. The channel 16 receives the first member 12 therein and encloses the same in a substantially secure manner.

In one preferred embodiment, first member 12 receives a coating with a particular fragrance through a dipping process wherein a fragrant media is in a liquid state and first member 12 is immersed therein. The liquid state is usually obtained through heating to a predetermined temperature as is known in the art. Upon removal of first member 12 from the fragrant media, excess media may be removed therefrom through agitation such that the interstices of first member 12 are not obscured thereby. The fragrant media forms a solid state as a result of the lowered temperature and is accordingly maintained upon first member 12. The fragrant media does not require further activation by manual or other means. Upon installation, a predetermined fragrance is emitted from the fragrant media.

Figure 8:
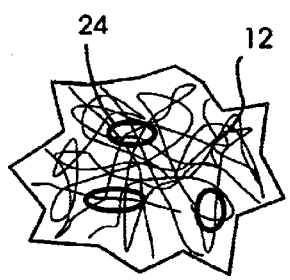
FIG. 8 is a partial frontal perspective view of the first member illustrating an alternate preferred embodiment incorporating fragrant elements.

Now also referring to FIG. 8, an alternate preferred embodiment is illustrated for incorporating at least a fragrant element 24 within first member 12. A plurality of fragrant elements 24 may be enclosed within two layers of first member 12 and maintained therein by the peripheral attachment of frame 14. The fragrant element 24 does not require further activation by manual or other means. Upon installation, a predetermined fragrance is emitted from the fragrant element 24. The size of the fragrant elements 24 may be used to dictate the length of time that the fragrance will emanate therefrom as determined by the surface-to-volume ratio. For example, the surface area (s) of a sphere is proportional to the square of the sphere's radius (r). The volume (v), however, is proportional to the cube of the radius (r). Accordingly, as spheres increase in volume, their surface area increases only as the ⅔ power of the volume, signifying that the increase in area is less than fully proportional to that in volume. Thus, bigger spheres have less surface area per unit of volume than little spheres and therefore bigger spheres sublimate at a lower rate than little spheres and last longer than little spheres.

Figure 4:
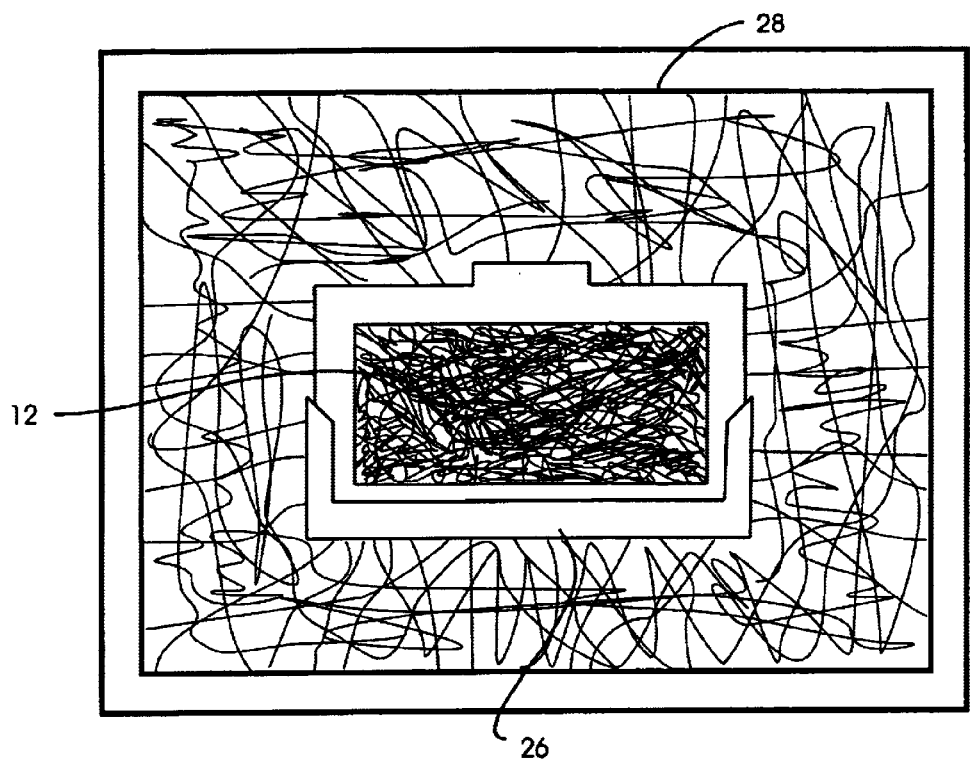
FIG. 4 is a frontal view of the scenting device mounted upon an air filter.

Now also referring to FIGS. 4, 5, and 6, in one preferred embodiment first member 12 is received within a mounting means 26 and is thereby attached to an air filter 28. However, it is to be understood that first member 12 may be attached directly to an air filter 28 via any means known within the art without departing from the essence of the present invention. Mounting means 26 is substantially "U" shaped and has an inwardly opening groove 30 which is adapted to slideably receive and securely, yet removably, maintain frame 14 of first member 12 therein. Mounting means 26 has an attaching means 32 thereon to attach mounting means 26 thereto. For purposes of illustration, but not limitation, attaching means 32 may be selected from any means known in the art such as hook and loop fasteners, "S" hook fasteners, pins, barbs, clips, clamps, adhesives, tapes, etc.

Use of the mounting means 26 facilitates the replacement of the scenting device 10 when the fragrance thereof is depleted. A user simply removes the depleted scenting device 10 from the mounting means 26 and inserts a new scenting device 10. Use of the mounting means 26 also prevents waste by not requiring replacement of the air filter 28 because only the scenting device 10 may no longer be fragrant. In addition, a scenting device 10 may be replenished by any means known in the art, whereby fragrance is applied directly to the first member 12 such that the same scenting device 10 may be reinserted into the mounting means 26.

Figure 7:
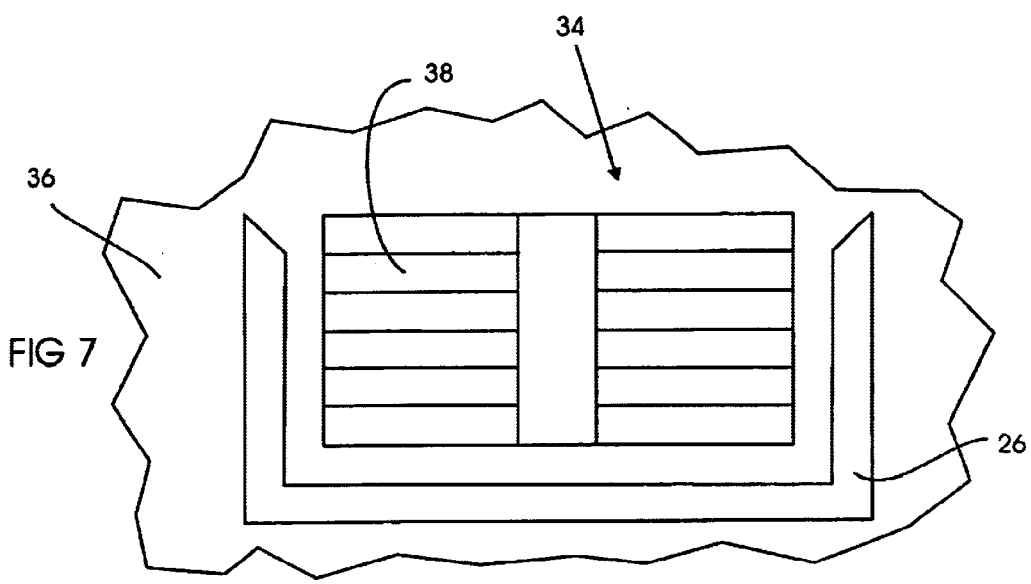
FIG. 7 is a frontal view of the mounting member illustrating one preferred installation thereof over an air outlet.

Now referring to FIG. 7, therein is illustrated a vent cover 34 that is adapted to function with scenting device 10. In one preferred embodiment, mounting means 26 may be attached to a first surface 36 such that the vent cover 34 is maintained within the opposing vertical sections of the "U" shaped mounting means 26. However, it is to be understood that mounting means 26 may be attached directly to vent cover 34 with the appropriate attaching means 32. Vent cover 34 has a plurality of slotted openings 38 which may alternate between a closed state and an open state at the desire of a user to either prevent or allow air flow respectively. Scenting device 10 may then be inserted into mounting means 26 as desired and can be exchanged with other scents and replaced upon depletion.

Now referring to FIG. 9, a modified vent cover 34 is illustrated that is adapted to receive scenting device 10 directly therein. Vent cover 34 has a planar front surface 40 having a plurality of slotted openings 38 thereon. Vent cover 34 is illustrated herein as having a substantially rectangular shape, however, it is to be understood that any other appropriate shape may be employed as determined by the surface onto which vent cover 34 is mounted. Accordingly, vent cover 34 may be modified to fit over an air conditioning or heating outlet in a home, place of business, and vehicles. In addition, the scenting device 10 may also be used with commercial or personal use hair dryers as described herein below.

A peripheral wall 42 extends substantially perpendicular to and in a rearward direction from front surface 40. A portion of peripheral wall 42 defines an aperture 44 which is shaped to accommodate scenting device 10. Upon installation, scenting device 10 traverses between opposing sides of the peripheral wall 42 such that first member 12 traverses slotted openings 38. In addition, frame 14 of scenting device 10 is received within aperture 44 and occludes the same when scenting device 10 is installed therein. To further maintain scenting device 10 within the peripheral wall 42, at least a retaining means 46 is provided on the peripheral wall 42 and traverses opposing sides thereof. Retaining means 46 is preferably an elongated member such as, but not limited to, an elastic band, a thread, a wire, or a rod. As a result, scenting device 10 is maintained within aperture 44 between retaining means 46 and the slotted openings 38. In addition, a control means 48 is provided on front surface 40 such that a user may alternate the slotted openings between a closed and open position to control the flow of air therethrough.

Now referring to FIG. 10, a hair dryer 50 as is known in the art is illustrated utilizing scenting device 10 is illustrated. Hair dryer 50 has an intake orifice 52 at a first end and an outlet orifice 54 at an end distal thereto. Scenting device 10 is preferably connected to the intake orifice 52 by the use of attaching means 32. Attaching means 32 allows secure yet removable attachment of device 10 to hair dryer 50 such that device 10 may easily be replaced upon expiration or when an alternate or no scent is desired. In addition, scenting device 10 may be used with hair dryers of a commercial nature which are usually found in beauty salons.

While the above description contains many specificities, these should not be construed as limitations on the scope of the invention, but rather as an exemplification of preferred embodiment thereof. Many other variations are possible without departing from the essential spirit of this invention. Accordingly, the scope of the invention should be determined not by the embodiments illustrated, but by the appended claims and their legal equivalents.

What is claimed is:

1. A scenting device for use with an airflow conduit, comprising
    a first member having a scent that does not require activation;
    a frame enclosing said first member at a periphery thereof; and
    an attaching means on said frame for attaching the device to the airflow conduit;
    whereby said first member traverses said frame.

2. The device of claim 1, wherein said scent is applied to said first member by immersing said first member in a liquid composition having said scent and upon withdrawal of the first member, said liquid solidifying upon said first member.

3. The device of claim 1, wherein said first member is comprised of a first layer and a second layer and at least a scenting element is maintained between said first layer and said second layer upon installation of said frame.

4. The device of claim 3, wherein said scenting element is spherical.

5. The device of claim 1, wherein said attaching means is selected from a group consisting of hook and loop fasteners, "S" hook fasteners, pins, barbs, clips, clamps, adhesives, and tapes.

6. The device of claim 1, wherein said attaching means is connected to an air filter within said airflow conduit selected from a group consisting of at least a heating, an air conditioning, and ventilating system.

7. The device of claim 1, wherein said attaching means is placed on the mounting means and the mounting means is thereby attached to an air flow conduit.

8. The device of claim 1, wherein said attaching means removably attaches said device to an inlet of an airflow based dryer means.

9. The device of claim 8, wherein said air flow based dryer means is a blow dryer and said inlet is an air intake opening.

10. The device of claim 7, wherein said mounting means is attached to a vent having a plurality of slotted openings such that said first member is maintained over said plurality of slotted openings.

11. A scenting device adapted for use in a heating, air conditioning, and ventilating system, the device comprising:
    a first member having a scent element not requiring activation by manual means;
    a frame enclosing said first member at a periphery thereof; and a mounting means removably receiving said frame therein, and said mounting means having an attaching means for attachment thereof to the heating, air conditioning, and ventilating system.

12. In combination, a scenting device having a scented, porous first member enclosed by a frame around a periphery thereof, and a vent cover for receiving the scenting device;
    the scenting device having a scent element not requiring manual activation;
    the vent cover further comprising a front surface, said front surface defining a plurality of slotted openings therein;
    a peripheral wall extending in a rearward direction from said front surface;
    an aperture being defined on a portion of said peripheral wall; whereby said aperture is adapted to receive the scenting device in a removable, yet secure, manner such that the frame occludes the aperture when the scenting device is installed.

13. The combination of claim 12, wherein the vent cover further comprises at least a retaining means that traverses across substantially opposing portions of said wall such that the scenting device is maintained between the front surface and said retaining means.

* * * * *

UNITED STATES PATENT AND TRADEMARK OFFICE
CERTIFICATE OF CORRECTION

| | | |
|---|---|---|
| PATENT NO. | : 6,749,672 B2 | Page 1 of 2 |
| APPLICATION NO. | : 09/846800 | |
| DATED | : June 15, 2004 | |
| INVENTOR(S) | : Cathy A. Lynn | |

It is certified that error appears in the above-identified patent and that said Letters Patent is hereby corrected as shown below:

At col. 5, l. 49, after "activation" insert the following:

--and said first member being porous;
said first member is a fibrous material consisting of at least fiber glass--

At col. 5, l. 51, after "thereof" insert the following:

--and said frame is made of a substantially rigid material selected from a group consisting of cardboard and plastic--

At col. 5, l. 52, delete the word "and".

At col. 5, l. 54, delete "conduit" and insert the following:

--conduit, said attaching means is connected to a mounting means having a substantially "U" shaped member having an inwardly opening groove of sufficient size to accommodate said frame in a slidingly removable manner--

At col. 6, l. 31, delete "means" and insert the following:

--means, and said first member is substantially porous to allow airflow therethrough--

At col. 6, l. 32, after "thereof;" insert the following:

--said frame is made of a substantially rigid material selected from a group consisting of cardboard and plastic--

At col. 6, l. 33, delete "and".

At col. 6, l. 33, before "mounting" insert the following:

--substantially rigid--

UNITED STATES PATENT AND TRADEMARK OFFICE
CERTIFICATE OF CORRECTION

PATENT NO. : 6,749,672 B2
APPLICATION NO. : 09/846800
DATED : June 15, 2004
INVENTOR(S) : Cathy A. Lynn It is certified that error appears in the above-identified patent and that said Letters Patent is hereby corrected as shown below:

At col. 6, l. 37, delete "system" and insert the following:

--system;
   said mounting means is substantially "U" shaped and has an inwardly opening groove of sufficient depth to accommodate said frame in a slidingly removable manner and having a tapered shape at upper ends of said "U" to allow insertion of said frame--

At col. 6, l. 42, delete "activation;" and insert the following:

--activation, and said first member is substantially porous to allow airflow
   therethrough;
said frame is made of a substantially rigid material;--

Signed and Sealed this

Twenty-first Day of July, 2009

JOHN DOLL
*Acting Director of the United States Patent and Trademark Office*